United States Patent [19]
Goldberg

[11] Patent Number: 5,824,693
[45] Date of Patent: Oct. 20, 1998

[54] METHOD FOR TREATMENT FOR PULMONARY DISEASE

[75] Inventor: Dennis I. Goldberg, Palatine, Ill.

[73] Assignee: Transcend Therapeutics, Inc., Cambridge, Mass.

[21] Appl. No.: 470,094

[22] Filed: Jun. 6, 1995

Related U.S. Application Data

[63] Continuation of Ser. No. 57,122, May 3, 1993, abandoned, which is a continuation of Ser. No. 830,554, Feb. 3, 1992, abandoned, which is a continuation of Ser. No. 639,275, Jan. 10, 1991, abandoned.

[51] Int. Cl.$^6$ .......................... A61K 31/425; A61K 31/13
[52] U.S. Cl. .......................... 514/365; 514/369; 514/667; 514/671
[58] Field of Search .................... 514/365, 369, 514/667, 671

[56] References Cited

U.S. PATENT DOCUMENTS

| | | | |
|---|---|---|---|
| 2,712,202 | 7/1955 | Hosler et al. | 47/57.5 |
| 3,737,536 | 6/1973 | Sagner et al. | 424/246 |
| 3,755,578 | 8/1973 | McFarland et al. | 424/246 |
| 4,175,130 | 11/1979 | Yamanaka et al. | 424/270 |
| 4,335,210 | 6/1982 | Meister et al. | 435/113 |
| 4,338,315 | 7/1982 | Paget et al. | 424/246 |
| 4,384,001 | 5/1983 | Gosalvez | 424/270 |
| 4,398,026 | 8/1983 | Takano | 544/133 |
| 4,420,479 | 12/1983 | Morwick et al. | 424/246 |
| 4,434,158 | 2/1984 | Meister | 424/94 |
| 4,438,124 | 3/1984 | Meister | 424/270 |
| 4,563,471 | 1/1986 | Satzinger et al. | 514/369 |
| 4,647,453 | 3/1987 | Meister | 424/54 |
| 4,647,571 | 3/1987 | Meister | 514/369 |
| 4,665,082 | 5/1987 | Meister et al. | 514/365 |
| 4,710,489 | 12/1987 | Meister | 514/18 |
| 4,752,618 | 6/1988 | Mascioli et al. | 514/549 |
| 4,775,675 | 10/1988 | Gyorgydeak et al. | 514/307 |
| 4,780,475 | 10/1988 | Cerra et al. | 514/408 |
| 4,784,685 | 11/1988 | Meister | 71/106 |
| 4,791,125 | 12/1988 | Clark | 514/369 |
| 4,798,835 | 1/1989 | Krupp et al. | 514/369 |
| 4,839,387 | 6/1989 | Poli | 514/19 |
| 4,868,114 | 9/1989 | Nagasawa et al. | 435/112 |
| 4,879,370 | 11/1989 | Meister | 530/331 |
| 4,963,577 | 10/1990 | Schorlemmer et al. | 514/369 |
| 5,002,953 | 3/1991 | Hindley | 514/275 |
| 5,028,627 | 7/1991 | Kilbourn et al. | 514/565 |
| 5,039,609 | 8/1991 | Klein | 435/68.1 |
| 5,053,387 | 10/1991 | Alexander | 514/2 |
| 5,055,446 | 10/1991 | Alexander et al. | 514/2 |
| 5,089,268 | 2/1992 | Katz | 424/450 |
| 5,095,027 | 3/1992 | Goldberg et al. | 514/369 |
| 5,158,883 | 10/1992 | Griffith | 435/240.2 |
| 5,208,249 | 5/1993 | Rowe et al. | 514/369 |
| 5,214,062 | 5/1993 | Mark et al. | 514/369 |

FOREIGN PATENT DOCUMENTS

| | | |
|---|---|---|
| 0-002 978 | 7/1979 | European Pat. Off. . |
| 0-257-992 | 3/1988 | European Pat. Off. . |
| 0-318 330 | 5/1989 | European Pat. Off. . |
| 0-327-263 | 8/1989 | European Pat. Off. . |
| 0-338-459 | 10/1989 | European Pat. Off. . |
| 0-373-002 | 6/1990 | European Pat. Off. . |
| 0-374-390 | 6/1990 | European Pat. Off. . |
| 0-415 598 | 3/1991 | European Pat. Off. . |
| 2296428 | 3/1976 | France . |
| 2141765 | 2/1991 | Germany . |
| 47 8537 | 1/1972 | Japan . |
| WO 91/14424 | 10/1991 | WIPO . |
| WO 93/11104 | 6/1993 | WIPO . |

OTHER PUBLICATIONS

Buhl, R., et al., 1990, Proc. Natl. Acad. Sci. 87:4063–4067.
Cooper, J.A.D., et al., 1989, J. Appl. Physiol. 67(6):2316–2322.
Transcend Therapeutics press release, dated March 20, 1998.
Abate et al., 1990, Science 249:1157–1161.
American College of Chest Physicians/Society of Critical Care Medicine Consensus Conference Committee, 1992, Critical Care Medicine 20(6):864–874.
Astor et al., 1988, Pharmac Ther pp. 115–121.
Bellin et al., 1987, J Dairy Sci 70:1913–1919.
Bernard et al., 1984, J Clin Invest 73:1772–1784.
Bielton et al., 1990, J Parenter Enteral Nutr 14(2):177–182.
Bone et al., 1992, Critical Care Medicine 20(6):724–725.
Bounous et al., 1989, Clinical Investigative Medicine 12(4):154–161.
Calvin et al., 1986, Gamete Research 14:265–275.
Chang et al., 1991,Toxicology 69(1):101–110.
Chung et al., 1990, American Institute of Nutrition pp. 158–165.
Cotgreave et al., 1988 Toxicology 50:331–343.
Cretton et al., 1990, Molecular Pharmacology 39:258–266.
Darley–Usmar et al., Free Radi Res Comm 7(3–6):247–254.
Duh et al., 1989, Proc Natl Acad USA 86:5974–5978.
Flaherty et al., 1988, Free Radical Biology and Medicine 5:409–419.
Frankova, 1967, Acla Vitro, Engl Ed 11(6):559–571.
Gordon et al., 1988, Journal of In Vitro Fertilization and Embryo Transfer 5(2):57–60.
Guarding Against Cellular Gutathione Deficiency, 1990, Nutrition Reviews, 48(9):346–348.
Gustafson et al., 1989, J Natl Cancer Inst. 81(16)1254–1258.
Handlon et al., 1987, Pharmaceutical Research 5(5):297–299.
Heinecke et al., 1987, J Biol Chem 262(21):10098–10103.

(List continued on next page.)

*Primary Examiner*—Theodore J. Criares
*Attorney, Agent, or Firm*—Pennie & Edmonds LLP

[57] ABSTRACT

The present invention provides a method for treating pulmonary disease. More specifically, the present invention provides a method for treating diseases such as adult respiratory distress syndrome which result in oxidative stress that damages the cells of the lung. Pursuant to present invention, a method is provided that increases the intracellular glutathione levels of at least the cells of the lungs of a patient with pulmonary disease. To this end, a non-cysteine substrate that is a precursor for the intracellular synthesis of glutathione is administered to the patient.

17 Claims, No Drawings

OTHER PUBLICATIONS

Jimenz et al., 1992, Cancer Investigation 10(4):271–276.
Kalebic et al., 1991, Proc Natl Acad Sci USA.
Keller et al., 1985, Arch Surg (Chicago) 120(8):941–945.
Kermici et al., 1990, Mechanisms for Aging and Development 53:73–84.
Kilbourn et al., 1992, Journal of the National Cancer Institute 84(13):1008–1016.
Kuzuya et al., 1989, Biochem Biophys Res Comm 163(3).
Lamperth et al., 1991, Laboratory Investigation 65(6):742–752.
Lassalle et al., 1992, J Reprod Fertil 95(2):313–324.
Levy et al., 1993, Proc Natl Acad Sci USA 19:9171–9175.
Lucht et al., 1987, Am J Med Sci 294(3):161–167.
Mandel et al., 1990, J Clin Invest 95(2):316–324.
Martenson et al., 1989, Proc Natl Acad Sci USA 86:5296–5300.
Martenson et al., 1989, Proc Natl Acad Sci USA 86:471–475.
Matsumoto et al., 1974, HCA Abstract 81:176108.
Mihm et al., 1991 Aids V(5):497–503.
Ministry of the Chemical Industry for Romania, 1970, HCA Abstract 73:80500.
Moslen, 1989, J Pharmacol Exp Ther, 248(1):157–163.
Nappe et al., 1989, J Soc Cosmet Chem 40:91–99.
Oerlu et al., 1990 Ger Offen 17.
Pacht et al., 1991, Chest 100(5):1397–1403.
Parthasarathy, 1987, Biochem Biophys Acta 917:337–340.
Passero et al., 1986, A Rev Respir Dis 133:A395.
Peristeris et al., 1992, Cell Immunol 140(2):390–399.
Perreault et al., 1988, Developmental Biology 125:181–186.
Perreault et al., 1984, Developmental Biology 101:160–167.
Perreault et al., 1987, Biology of Reproduction 36:239–244.
Pruche et al., 1991, International Journal of Cosmetic Science 13:117–124.
Rao et al., 1992, Int J Peptide Protein Res 40:507–514.
Reyes et al., 1989, Gamete Research 23:39–47.
Roberts et al., 1987, J Med Chem 30(10):1891–1896.
Roederer et al., 1990, Proc Natl Acad Sci USA 87:4884–4888.
Roseneld et al., 1991, The American Society for Clinical Investigation 87:90–99.
Schnittman et al., 1989, Science 245:305–308.
Shapiro, 1991, Science 533–536.
Slaweta et al., 1987, Amin Reprod Sci 13(4):249–253.
Smith et al., 1990, Am Rev Respir Dis 141:149.
Sporn et al., 1990, American Journal of Respiratory Cell and Molecular Biology 2(1):81–90.
Staal et al., 1990, Proc Natl Acad USA 87:9943–9947.
Stevens, 1989, Microbiological Reviews pp. 318–332.
Strausz et al., 1990, Am Rev Respir Dis 141:124–128.
Sun et al., 1988, Exp Mol Path 49:254–266.
Suthanthiran et al., 1990, Proc Natl Acad Sci 37:3343–3347.
Tsan et al., 1985, Biochem Biophys Res Comm 127(1):270–276.
Tsan et al., 1988, Inflammation 12(2):113–121.
Uhlig et al., 1990, Glutathione Enhancement in Various Mouse Organs and Protection by Glutathione Isopropyl Ester Against Liver Injury, p. 1877.
Wellner et al., 1984, Proc Natl Acad Sci USA 81:4732–4735.
Zirkin et al., 1985, Gamete Research 11:349–365.
Anderson et al., 1985, Arch Biochem and Biophys 239:538–548.
Bernard et al., 1989, Am Rev Respir Dis 139:A221.
Cooper and Merrill, 1989, J Appl Physiol 67:2316–2322.
Cotgreave et al., 1986, Bull Eur Physiopathol Respir 22:263–266.
Pacht et al., 1991, Chest 100:1397–1403

METHOD FOR TREATMENT FOR PULMONARY DISEASE

CROSS-REFERENCE TO RELATED APPLICATIONS

This application is a continuation of application Ser. No. 08/057,122, filed May 3, 1993, now abandoned, which is a continuation of application Ser. No. 07/830,554, filed Feb. 3, 1992, now abandoned, which is a continuation of application Ser. No. 07/639,275 filed Jan. 10, 1991, now abandoned.

BACKGROUND OF THE INVENTION

The present invention relates generally to the treatment of pulmonary disease. More specifically, the present invention relates to the treatment of diseases that result in acute and/or chronic respiratory distress.

There are a number of pulmonary or respiratory disease states that can cause acute or chronic respiratory distress and result in damage to the lungs of the patient. Resulting damage can be debilitating to the patient and on occasion result in death.

Adult respiratory distress syndrome (ARDS) is a common medical emergency that is precipitated by a variety of acute processes that directly or indirectly injure the lungs. For example, ARDS can be precipitated by primary bacterial or viral pneumonias, aspiration of gastric contents, direct chest trauma, prolonged or profound shock, burns, near drowning, fat embolism, blood transfusions, cardio-pulmonary bypass, $O_2$ toxicity, or acute hemorrhagic pancreatitis. ARDS usually develops within twenty-four to forty-eight hours after initial injury or illness. It is believed that activated leukocytes and platelets accumulate in the capillaries, interstitium, and airspaces. They may release products including prostaglandins, toxic $O_2$ radicals, proteolytic enzymes, and other mediators that injure cells, promote fibrosis, and alter bronchomotor tone and vasoreactivity. See, *The Merck Manual*, Fifteenth Edition.

Injury to the pulmonary capillary endothelium and alveolar epithelium causes plasma and blood to leak into the interstitial and intra-alveolar spaces. Flooding of the alveolae and atelectasis results. Typically, within two or three days, a second phase of lung injury is characterized by bronchoalveolar inflation. Additionally, there is proliferation of epithelial and interstitial cells. Typically, in a third phase collagen accumulation may progress rapidly. This can result in severe interstitial fibrosis within two to three weeks. This pathological change, can lead to low lung compliance, pulmonary hypertension, decreased functional residual capacity, ventilation/perfusion maldistribution, and hypoxemia.

Unfortunately, the survival rate for severe ARDS is less than 50% with appropriate treatment. Although the mechanism of lung injury in adult respiratory distress syndrome is not certain, data from animal models and indirect evidence from studies in human beings has suggested that toxic oxygen metabolites produced by stimulated neutrophils are a possible agent of the alveolar injury. Baldwin, et al., *Oxidant Activity In Expired Breath of Patients With Adult Respiratory Distress Syndrome*, The Lancet, Jan. 4, 1986, pages 11–13.

Because it has been hypothesized that oxygen free radicals released during endotoxemia may contribute to the lung injury of ARDS, the effect of intravenous n-acetylcysteine, a free radical scavenger, on the endotoxin induced model of ARDS in awake sheep has been investigated. Bernard, et-al., *Effect of N-acetylcysteine on the Pulmonary Response to Endotoxin in the Awake Sheep and Upon In Vitro Granulocyte Function*, J. Clin. Invest., Vol. 73, pp 1772–84 (1984). The paper states that n-acetylcysteine inhibits granulocyte aggregation and scavenges free radicals in vitro. The paper postulates, therefore, that the beneficial effect of n-acetylcysteine in attenuating the pathophysiologic processes seen in the sheep model of the adult respiratory syndrome is due to its ability to scavenge oxygen free radicals in vivo.

Lucht, et al., *Prevention of Release of Granulocyte Aggregants Into Sheep Lung Lymph Following Endotoxemia By Acetylcysteine*, The American Journal of the Medical Sciences, Vol. 294 No. 3 (September 1987), discusses experiments wherein n-acetylcysteine was administered to sheep before endotoxin infusion. The paper concludes that endotoxemia causes the release from the lungs of substance (s) that activate granulocytes, and that this response is prevented by n-acetylcysteine, possibly as a result of the antioxidant properties of the drug.

Although, attention has focused on treating and/or curing ARDS, an effective treatment is still not available.

Infant respiratory distress syndrome, or IRDS, is a disorder primarily of prematurity, manifested clinically by respiratory distress and pathologically by pulmonary hyaline membrane disease and atelectasis. See *Merck Manual*, Fifteenth Edition. IRDS results from diffuse lung atelectasis due to a deficiency of pulmonary surfactants at birth. Due to pulmonary insufficiency, these neonates are placed in hyperoxic (95% $O_2$) environments. The inability to produce adequate amounts of glutathione exacerbates the oxidative stress and damage to the lungs. If untreated, IRDS can result in bronchopulmonary displasia, blindness, brain damage, multiple organ failure and death.

Other disease states, such as cystic fibrosis, idiopathic pulmonary fibrosis, and emphysema, also can result in lung damage due to cell damage from oxidation. The lungs are exposed to oxidative stress due to airborne oxidants and to hyperoxygen stress when respiratory treatment includes elevated oxygen (e.g., 95% $O_2$) treatment. Additionally, inflammatory cells, macrophages, neutrophils, and the like, secrete active oxygen species in the lungs.

SUMMARY OF THE INVENTION

The present invention relates to a method for treating pulmonary disease. Specifically, the present invention relates to a method for treating pulmonary disease by increasing the intracellular synthesis of glutathione. The method includes the step of administering to a patient a non-cysteine glutathione precursor that will stimulate the intracellular synthesis of glutathione.

It has been found, that by increasing glutathione levels within a cell, the pulmonary cells will experience reduced damage when exposed to oxidative stress. Cells having depressed glutathione levels are susceptible to membrane lipid peroxidation, mitochandrial damage, and progressive fibrosis of lung tissue. However, turnover of glutathione and of endogenous antioxidants in pulmonary endothelium is very rapid.

In an embodiment of the present invention, L-2-oxothiazolidine-4-carboxylate is utilized to elevate tissue glutathione levels. In another embodiment, glutathione esters are utilized to elevate glutathione levels within the cells.

In a further embodiment of the invention, the present invention provides a method for treating adult respiratory distress syndrome comprising the step of administering to a patient having adult respiratory stress syndrome, a sufficient amount of a non-cysteine substrate to elevate the intracellular level of glutathione, at least in the lungs, of a patient.

In an embodiment, the non-cysteine substrate is administered parenterally.

In an embodiment of the present invention, the non-cysteine substrate is administered enterally.

Additional features and advantages of the present invention are described in, and will be apparent from, the detailed description of the presently preferred embodiments.

DETAILED DESCRIPTION OF THE PRESENTLY PREFERRED EMBODIMENTS

The present invention provides a method for treating pulmonary disease. More specifically, the present invention provides a method for treating diseases such as adult respiratory distress syndrome and infant respiratory distress syndrome which result in oxidative stress that can damage the cells of the lung.

Pursuant to the present invention, a method is provided that increases the intracellular glutathione levels of at least the cells of the lungs of a patient with pulmonary disease. It has been found that in acute respiratory distress syndromes glutathione levels of many patients are suppressed. Due to the suppressed levels of glutathione, oxidative stress can occur that damages the lung cells.

Pursuant to the present invention, a non-cysteine substrate that is a precursor for the intracellular synthesis of glutathione is administered to the patient. Because the substrate is not a cysteine substrate, a more effective tissue distribution of the substrate occurs within the patient. It is believed that the enzymes necessary for deacetylization of an acetylated compound such as n-acetylcysteine exist only in the kidney. Accordingly, a compound such as n-acetylcysteine must be metabolized to cysteine in the kidney then transported to the liver or peripheral cells. Therefore, such compounds may not be sufficiently distributed to the requisite tissues of the patient, i.e., the tissue of the lungs.

Furthermore, because the present invention provides a non-cysteine substrate the compound is not itself an antioxidant. Although it may be desireable to introduce an anti-oxidant into a patient having adult respiratory distress syndrome to prevent damage from the oxygen radicals, anti-oxidants are not stable.

Pursuant to the present invention any non-cysteine substrate that stimulates intracellular glutathione synthesis can be utilized. Preferably, the method comprises the step of administering an agent chosen from the group consisting of L-2-oxothiazolidine-4-carboxylate and glutathione esters. However, other thiazolidine-4-carboxylate analogs that are converted intracellulary to glutathione can be utilized.

L-2-oxothiazolidine-4-carboxylate, in vitro, is subjected to the action of 5-oxo-L-prolinase in the presence of adenosine triphosphate to produce S-carboxyl cysteine. S-carboxyl cysteine is then decarboxylated to produce cysteine. Cysteine is then metabolized to provide glutathione. See, U.S. Pat. Nos.: 4,335,210; 4,434,158; 4,438,124; 4,665,082; and 4,647,571 the disclosures of which are incorporated herein by reference.

As previously stated, the non-cysteine substrate can include a glutathione ester. For example, the compound can have the structure:

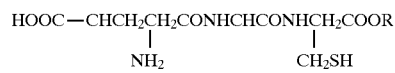

wherein R is an alkyl group containing 1 to 10 carbon atoms. Preferably, the methyl and ethyl glutathione esters are used. It is also preferred to use glutathione isopropyl ester. Glutathione esters are disclosed in U.S. Pat. No. 4,784,685, the disclosure of which is incorporated herein by reference.

In an embodiment of the invention, the composition of the present invention includes: 3% L-2-oxothiazolidine-4-carboxylate in a phosphate buffer. Additional embodiments include:

a) A buffered (pH 6.5–6.8) 3% or 6% L-2-oxothiazolidine-4-carboxylate or glutathione ester aqueous solution.

b) A buffered 3% or 6% L-2-oxothiazolidine-4-carboxylate or glutathione ester aqueous solution containing any of the following, alone or in appropriate combinations: amino acids, dextrose or other carbohydrate sources, and lipid emulsions.

c) A vial containing a crystalline or lyophilized non-cysteine glutathione precursor to which appropriate aqueous solutions are added at time of use.

d) A gelatin capsule containing a crystalline or lyophilized non-cysteine glutathione precursor.

e) A pill containing a crystalline or lyophilized non-cysteine glutathione precursor.

f) A liquid elemental, protein hydrolysate, carbohydrate and/or lipid emulsion containing enteral dietary supplement containg a non-cysteine glutathione precursor.

The composition can be administered as an adjunct therapy with other typical therapies. For example, steroids, non-steroid anti-inflammatories, prostaglandin synthesis inhibitors (ibuprofen), mucolytics, tumor necrosis factor antibodies, artificial surfactants (Exosurf, Survanta), hyperoxic and ventilation therapies, and antibiotics can be administered with the present invention.

By way of example, but not limitation, contemplated examples of the present invention will now be given.

EXAMPLE 1

A 55-year-old patient with sepsis syndrome that progressed into ARDS was given an intravenous administration of a neutral (pH 6.5–6.8) 6% solution of L-2-oxothiazolidine-4-carboxylate equivalent to 15 mg/kg, t.i.d. for 10 days. It should be noted that a continuous infusion of a 6% solution equivalent to 45 mg/kg/day could have been used as an alternative dosing regimen. The infusion although by independent intravenous administration, could have been through an indwelling intravenous catheter.

The patient demonstrated the following physiological characteristics at the start and end of treatment:

| Physiology | Start | End |
|---|---|---|
| PaO$_2$/PAO$_2$ | 0.24 | 0.38 |
| Cardiac Output (liters/min) | 5.65 | 7.93 |
| Thoracic Static Compliance (ml/cm H$_2$O) | 34.4 | 42.3 |
| Chest Radiograph of Pulmonary Edema (0 = normal, 3 = severe) | 2.5 | 1.1 |
| Plasma Glutathione (nmoles/ml,) | 2.47 | 7.96 |
| Red Cell Glutathione (nmoles/ml) | 2,753 | 5,825 |

-continued

| Physiology | Start | End |
|---|---|---|
| Lung Glutathione (nmoles/ml by Bronchoalveolar lavage) | 84 | 398 |

EXAMPLE 2

A neonate born at 27 weeks gestational age, weighing 984 grams, and suffering from Hyaline membrane disease was placed in a ventilator and given Exosurf (95 cc/kg) at 18 and 30 hrs of age. The patient received an intravenous administration of a neutral (Ph 6.5–6.8) 3% L-2-oxothiazolidine-4-carboxylate equivalent to 15 mg/kg, t.i.d., as a continuous infusion. A 6% solution equivalent to 45 mg/kg could have also been administered. The administration was continued until the infant has sufficiently developed to demonstrate adequate blood oxygenation in a normoxic environment, without mechanical or artificial ventilatory support.

The neonate displayed the following ventilatory requirements at entry and at 28 days:

|  | Entry | Day 28 |
|---|---|---|
| Oxygenation index | 1.48 | 0.62 |
| Ventilation rate | 920/24 hr | 223 |
| FiO$_2$ | 1184/24 hr | 774 |
| Positive end—expiratory pressure | 104/24 hr | 31 |
| Mean airway pressure | 208/24 hr | 56 |

(Values are summation of area under curve for 24 hour measurements).

At 28 days the patient was scored 1.5 for bronchopulmonary displasia, 1.0 for retrolental fibroplasia and 0.5 for intraventricular hemorrhage on a 0 to 5 scale (0 being normal, 5 being severe).

EXAMPLE 3

An 18-year-old hospitalized cystic fibrosis patient received intravenous tobramycin and ceftazidine every eight hours for 6 days. The patient received an intravenous administration of a neutral (pH 6.5–6.8) 3% L-2-oxothiazolidine-4-carboxylate equivalent to 15 mg/kg, t.i.d. during continuous infusion. Alternatively, a 6% solution equivalent could have been administered. Although administration occurred during in-patient treatment it could have occurred using home intravenous drug therapy. Administration of the non-cysteine glutathione precursor occured by independent injection at infusion, but could have taken place by infusion through an indwelling intravenous catheter.

The following changes in physiological characteristics were recorded at termination of treatment;

| SaO$_2$ | +3.6% |
|---|---|
| Weight (% increase) | +4.5% |
| FVC (% predicted) | +15.9% |
| FEV1 (% predicted) | +14.3% |
| Bronchoalveolar lavage glutathione | +322% |

The patient with cystic fibrosis also receive an enteral dose of the non-cysteine glutathione precursor equivalent to 15 mg/kg, t.i.d., as a prophylactic treatment during periods free of acute respiratory infection. The enteral dose was given as a capsule, but could have been given as a pill, liquid, or as part of a nutrient containing liquid enteral diet, or as a combination of these delivery methods.

EXAMPLE 4

A 68-year-old malnourished patient with an acute exacerbation of emphysema is admitted to the respiratory ICU. The patient requires mechanical ventilation and nutritional support. An enteral diet containing 18% protein, 27% CHO, 55% fat is provided at 1.3 times the resting energy expenditure. The diet was supplemented with 15 mg/kg of a non-cysteine glutathione precursor in 250 ml of diet. The patient was successfully weaned from the ventilator and diet on day 8. Lung lavage glutathione levels were taken at admission and on day 7:

|  | Admission | Day 7 |
|---|---|---|
| PaCO$_2$ | 6.09 | 5.15 |
| PaCO$_2$/PAO$_2$ | 31.5 | 38.4 |
| Ventilation rate (b/m) | 31 | 24 |
| Minute volume (l/m) | 16.5 | 14.2 |
| Glutathione (umol/ml) | 95 | 402 |

It is anticipated that a patient with emphysema would receive an enteral dose of a non-cysteine glutathione precursor equivalent to 15 mg/kg, t.i.d., during periods of acute exacerbations, and as a prophylactic treatment during quiescent periods. The enteral dose could be given as a capsule, pill, liquid, or as part of a nutrient containg liquid enteral diet, or as a combination of these delivery methods.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim as our invention:

1. A method for treating a human in need thereof and at risk of acute respiratory distress syndrome precipitated by primary bacterial or viral pneumonia, aspiration of gastric contents, direct chest trauma, prolonged or profound shock, burns, near drowning, fat embolism, blood transfusion, cardiopulmonary bypass or acute hemorrhagic pancreatitis comprising administering to the human a glutathione ester in an amount sufficient to reduce the risk of acute respiratory distress syndrome in the human in need thereof.

2. A method for treating a human in need thereof and at risk of acute respiratory distress syndrome precipitated by primary bacterial or viral pneumonia, aspiration of gastric contents, direct chest trauma, prolonged or profound shock, burns, near drowning, fat embolism, blood transfusion, cardiopulmonary bypass or acute hemorrhagic pancreatitis comprising administering to the human a compound selected from the group consisting of L-2-oxothiazolidine-4-carboxylate and L-2-oxothiazolidine-4-carboxylic acid in an amount sufficient to reduce the risk of acute respiratory distress syndrome in the human in need thereof.

3. A method for treating acute respiratory distress syndrome precipitated by primary bacterial or viral pneumonia, aspiration of gastric contents, direct chest trauma, prolonged or profound shock, burns, near drowning, fat embolism, blood transfusion, cardiopulmonary bypass or acute hemorrhagic pancreatitis comprising administering to a human having acute respiratory distress syndrome a glutathione ester in an amount sufficient to improve the pulmonary function of the human in need thereof.

4. A method for treating acute respiratory distress syndrome precipitated by primary bacterial or viral pneumonia, aspiration of gastric contents, direct chest trauma, prolonged or profound shock, burns, near drowning, fat embolism, blood transfusion, cardiopulmonary bypass or acute hemorrhagic pancreatitis comprising administering to a human having acute respiratory distress syndrome a compound selected from the group consisting of L-2-oxothiazolidine-4-carboxylate and L-2-oxothiazolidine-4-carboxylic acid in an amount sufficient to improve the pulmonary function of the human in need thereof.

5. A method for treating acute respiratory distress syndrome precipitated by primary bacterial or viral pneumonia, aspiration of gastric contents, direct chest trauma, prolonged or profound shock, burns, near drowning, fat embolism, blood transfusion, cardiopulmonary bypass or acute hemorrhagic pancreatitis comprising administering to a human having acute respiratory distress syndrome a glutathione ester in an amount sufficient to prevent multiple organ dysfunction or failure in the human in need thereof.

6. A method for treating acute respiratory distress syndrome precipitated by primary bacterial or viral pneumonia, aspiration of gastric contents, direct chest trauma, prolonged or profound shock, burns, near drowning, fat embolism, blood transfusion, cardiopulmonary bypass or acute hemorrhagic pancreatitis comprising administering to a human having acute respiratory distress syndrome a compound selected from the group consisting of L-2-oxothiazolidine-4-carboxylate and L-2-oxothiazolidine-4-carboxylic acid in an amount sufficient to prevent multiple organ dysfunction or failure in the human in need thereof.

7. A method for reducing oxidative damage to lung tissue precipitated by primary bacterial or viral pneumonia, aspiration of gastric contents, direct chest trauma, prolonged or profound shock, burns, near drowning, fat embolism, blood transfusion, cardiopulmonary bypass or acute hemorrhagic pancreatitis comprising administering to a human in need thereof and at risk of oxidative damage to lung tissue a glutathione ester in an amount sufficient to reduce oxidative damage in lung tissue of the human in need thereof.

8. A method for reducing oxidative damage to lung tissue precipitated by primary bacterial or viral pneumonia, aspiration of gastric contents, direct chest trauma, prolonged or profound shock, burns, near drowning, fat embolism, blood transfusion, cardiopulmonary bypass or acute hemorrhagic pancreatitis comprising administering to a human in need thereof and at risk of oxidative damage to lung tissue a compound selected from the group consisting of L-2-oxothiazolidine-4-carboxylate and L-2-oxothiazolidine-4-carboxylic acid in an amount sufficient to reduce oxidative damage in lung tissue of the human in need thereof.

9. A method for reducing oxidative damage to lung tissue precipitated by sepsis comprising administering to a human in need thereof and at risk of oxidative damage to lung tissue a glutathione ester in an amount sufficient to reduce oxidative damage in lung tissue of the human in need thereof.

10. A method for reducing oxidative damage to lung tissue precipitated by sepsis comprising administering to a human in need thereof and at risk of oxidative damage to lung tissue a compound selected from the group consisting of L-2-oxothiazolidine-4-carboxylate and L-2-oxothiazolidine-4-carboxylic acid in an amount sufficient to reduce oxidative damage in lung tissue of the human in need thereof.

11. A method for treating acute respiratory distress syndrome precipitated by sepsis comprising administering to a human having acute respiratory distress syndrome a glutathione ester in an amount sufficient to improve the pulmonary function of the human in need thereof.

12. A method for treating acute respiratory distress syndrome precipitated by sepsis comprising administering to a human having acute respiratory distress syndrome a compound selected from the group consisting of L-2-oxothiazolidine-4-carboxylate and L-2-oxothiazolidine-4-carboxylic acid in an amount sufficient to improve the pulmonary function of the human in need thereof.

13. A method for treating acute respiratory distress syndrome precipitated by sepsis comprising administering to a human having acute respiratory distress syndrome a glutathione ester in an amount sufficient to prevent multiple organ dysfunction or failure in the human in need thereof.

14. A method for treating acute respiratory distress syndrome precipitated by sepsis comprising administering to a human having acute respiratory distress syndrome a compound selected from the group consisting of L-2-oxothiazolidine-4-carboxylate and L-2-oxothiazolidine-4-carboxylic acid in an amount sufficient to prevent multiple organ dysfunction or failure in the human in need thereof.

15. A method for treating a human in need thereof and at risk of acute respiratory distress syndrome precipitated by sepsis comprising administering to the human a glutathione ester in an amount sufficient to reduce the risk of acute respiratory distress syndrome in the human in need thereof.

16. A method for treating a human in need thereof and at risk of acute respiratory distress syndrome precipitated by sepsis comprising administering to the human a compound selected from the group consisting of L-2-oxothiazolidine-4-carboxylate and L-2-oxothiazolidine-4-carboxylic acid in an amount sufficient to reduce the risk of acute respiratory distress syndrome in the human in need thereof.

17. The method according to claim 7, 1, 9, 3, 5, 11, 13 or 15, wherein the glutathione ester is selected from the group consisting of glutathione alkyl esters wherein the alkyl group contains 1 to 10 carbon atoms.

* * * * *